United States Patent
Nisivoccia

(10) Patent No.: US 11,944,564 B2
(45) Date of Patent: Apr. 2, 2024

(54) TRACTION SYSTEM

(71) Applicant: Glen Nisivoccia, Mokena, IL (US)

(72) Inventor: Glen Nisivoccia, Mokena, IL (US)

(*) Notice: Subject to any disclaimer, the term of this patent is extended or adjusted under 35 U.S.C. 154(b) by 466 days.

(21) Appl. No.: 17/241,440

(22) Filed: Apr. 27, 2021

(65) Prior Publication Data
US 2021/0338470 A1    Nov. 4, 2021

Related U.S. Application Data

(60) Provisional application No. 63/018,813, filed on May 1, 2020.

(51) Int. Cl.
*A61F 5/042* (2006.01)
*A61F 5/055* (2006.01)

(52) U.S. Cl.
CPC .............. *A61F 5/042* (2013.01); *A61F 5/055* (2013.01)

(58) Field of Classification Search
CPC .. A61F 5/042; A61F 5/055; A61F 5/05; A61F 5/04; A61F 5/01; A61F 5/00; A61F 5/05883; A61F 5/058; A61F 5/05816; A61F 5/3738; A61F 5/048
See application file for complete search history.

(56) References Cited

U.S. PATENT DOCUMENTS

| | | | | |
|---|---|---|---|---|
| 4,043,325 A * | 8/1977 | Ochs | ...................... | A61F 5/055 602/18 |
| 4,407,274 A * | 10/1983 | Goodley | .............. | A61H 1/0218 606/241 |
| 5,403,266 A | 4/1995 | Bragg et al. | | |
| 10,744,024 B2 | 8/2020 | Senyei et al. | | |
| 2002/0169401 A1 * | 11/2002 | Walpin | ................... | A61F 5/055 602/18 |
| 2009/0306567 A1 * | 12/2009 | Meyer | .................. | A61H 1/0218 602/33 |
| 2016/0058600 A1 * | 3/2016 | Basill | ..................... | A61F 5/055 602/18 |

OTHER PUBLICATIONS

Scrip Hessco, 2016 chiropractic catalog images, published in 2016.

* cited by examiner

*Primary Examiner* — Tarla R Patel
(74) *Attorney, Agent, or Firm* — Arenberg Goldgehn Davis & Garmisa

(57) ABSTRACT

The present system generally relates to a therapy device for applying traction to a patient's head and neck. A collar includes a fastener that secures the collar in a ring shape. It is provided with straps that extend from an exterior circumference of the ring. The collar may be positioned around a patients neck such that applying a traction force to the straps translates that force to the collar which in turn applies force to the underside of the patient's jaw and to the base of the patient's skull and thereby applies traction therapy to the patient's neck.

14 Claims, 6 Drawing Sheets

TRACTION SYSTEM

CROSS-REFERENCE

This application claims priority to U.S. Provisional Patent Application No. 63/018,813 filed on May 1, 2020 on behalf of Glen John Nisivoccia, the entirety of which is incorporated herein by this reference for all purposes.

BACKGROUND OF THE INVENTION

In practicing chiropractic medicine, it is often helpful to patients to apply neck traction. Administering traction to the head and neck region is difficult in that there are no easily graspable areas on the head or neck to apply long term pressure in a comfortable manner for the patient. In the past, traction devices have relied on placing a sling or cup underneath the chin of a patient, sometimes in conjunction with a strap that surrounds the patient's head or that extends from the chin to a cup at the back of the skull. However, such systems apply undue pressure to one or more of the front of the jaw and mandibular joint, which can have adverse effects on those areas of the body and thus provide sub-optimal therapy. Thus, there is a need for a neck traction device that apples traction therapy to the head and neck in a comfortable manner and without applying undue pressure on the joint of jaw.

SUMMARY OF THE PRESENT SYSTEM

The present system provides a simple solution. The system includes a cervical collar that surrounds the neck. The collar may vary in its height about its circumference. The collar may be made of a single strip that includes a fastener, such as mating hook and loop fastening system, snaps, laces or similar fastener on either end. The fastener fastens the ends together to form a circular collar. While it is conceivable that the collar could have any width, it was found that a collar having a width of approximately one to two inches provides a comfortable user experience when traction force was applied to the device. The collar may be constructed of foam. In some embodiments, the foam is covered with an outer cover. The cover may be made of a fabric, vinyl, naugahyde, leather, plastic, or other pliable material suitable for contact with human skin. The cover may be permanently affixed to the foam collar, such as by sewing the foam within the cover. Alternatively, the cover may form a pocket and be removable so that the cover can be separately laundered. It should be appreciated that the foam and cover collectively may be referred to as the collar.

The collar is provided with a plurality of straps. For example, two straps may be affixed to the exterior circumference of the collar. The collar may fasten together at the back, have a dip in the front, and two raised sides. One strap may be affixed to the exterior of one side, while a second strap may be affixed to the other side. Each strap may be positioned such that it extends up, perpendicular to a circumferential plane of the collar. In one embodiment, not considering the fastener, when laid flat, the collar with the straps is symmetrical about a vertical central axis. The straps may include a proximal end that is affixed to the collar, such as by sewing the proximal end to the cover of the collar, and a distal end. The distal end may terminate in loops or include rings, such as D-rings.

In use, a doctor may wrap the collar around the patient's neck and secure the fastener(s). For embodiments having a variable height, such as an embodiment with a front dip, the collar may be positioned such that the front dip is positioned under the body (or base mandible) of the jaw, behind the mental protuberance but in front of angle of the ramus. The distal ends of the straps may be brought together above the head. As the collar wraps around the neck, it can be fit snuggly against the neck such that it contacts the soft tissue on the inside portion of the jaw (proximal to the mylohyoid and digastric muscles and salivary glands). Traction force may be applied to the distal ends of the straps which is translated by the collar to distributed force across the neck, skull, and soft tissue on the inside portion of the jaw. Because the front of the collar is positioned snuggly around the neck, the traction force is directed primarily through the soft tissue rather than directly focusing on the base mandible. That limits pressure on the bone and relieves stress that prior systems place on the mandibular joint. Because the collar surrounds the neck, the back of the collar simultaneously translates the traction force to the external occipital protuberance. Together, the front and back of the collar pull the head away from the body such that the neck experiences the tension of the traction force. Thus the collar is able to apply comfortable traction force to the neck and head without pulling the chin back (and thus placing strain on the temporomandibular joint) or squeezing the skull.

Further embodiments are set forth in more detail below with reference to the drawings.

DETAILED DESCRIPTION OF PREFERRED EMBODIMENTS

Figure 1:
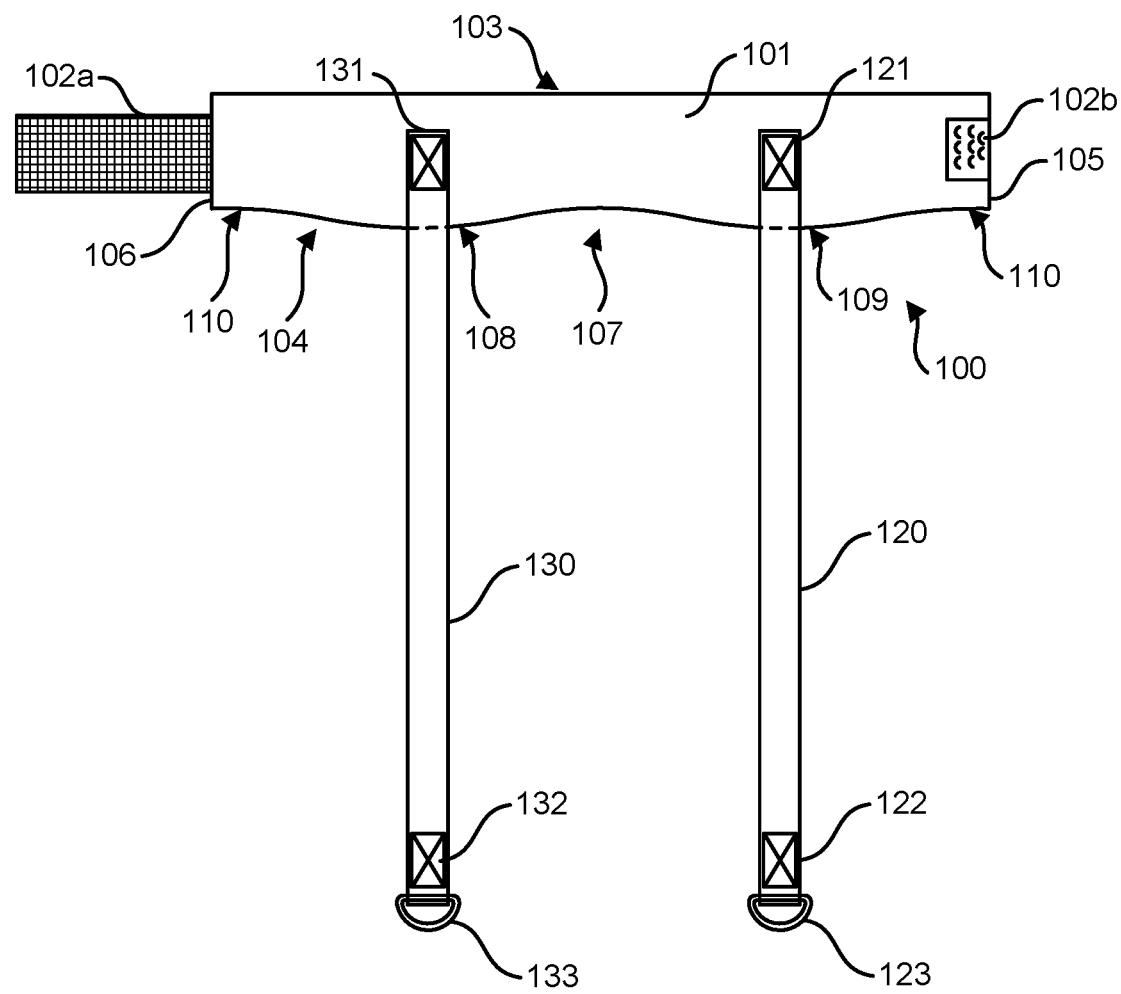
FIG. 1 is a plan view of an embodiment of the present system with the fastener unfastened.

The preferred embodiments of the present invention are described with reference to the drawings below. In the drawings, like numbers are used to refer to like elements. Unless otherwise stated, "and" is conjunctive, while "or" is disjunctive and conjunctive such that the condition "A or B" is satisfied by any of "A" alone, "B" alone, and "A and B" together.

Figure 6:
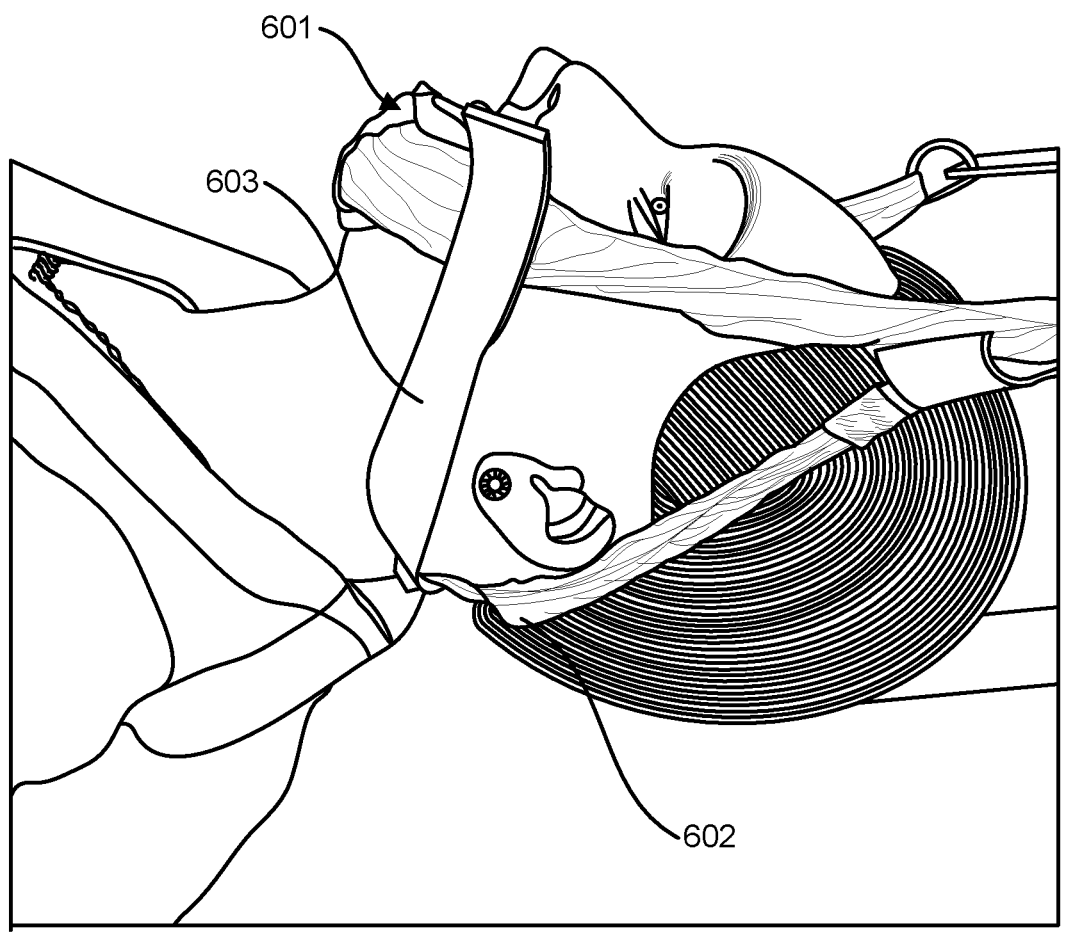
FIG. 6 is a view of the prior art.

FIG. 6 is a depiction of a prior art system. The prior art system includes a front strap 601 cups and pulls the jaw, applying force to the jaw bone and mandibular joint. A sling 602 at the back wraps around the base of the skull. A securing strap 603 is provided on either side of the harness to prevent the straps 601, 602 from separating too far and slipping off the patient's head. However, the securing straps to not directly apply traction force to the patient. The relatively thin fabric used creates lines of pressure at the edges which can lead to discomfort for patients.

Figure 2:
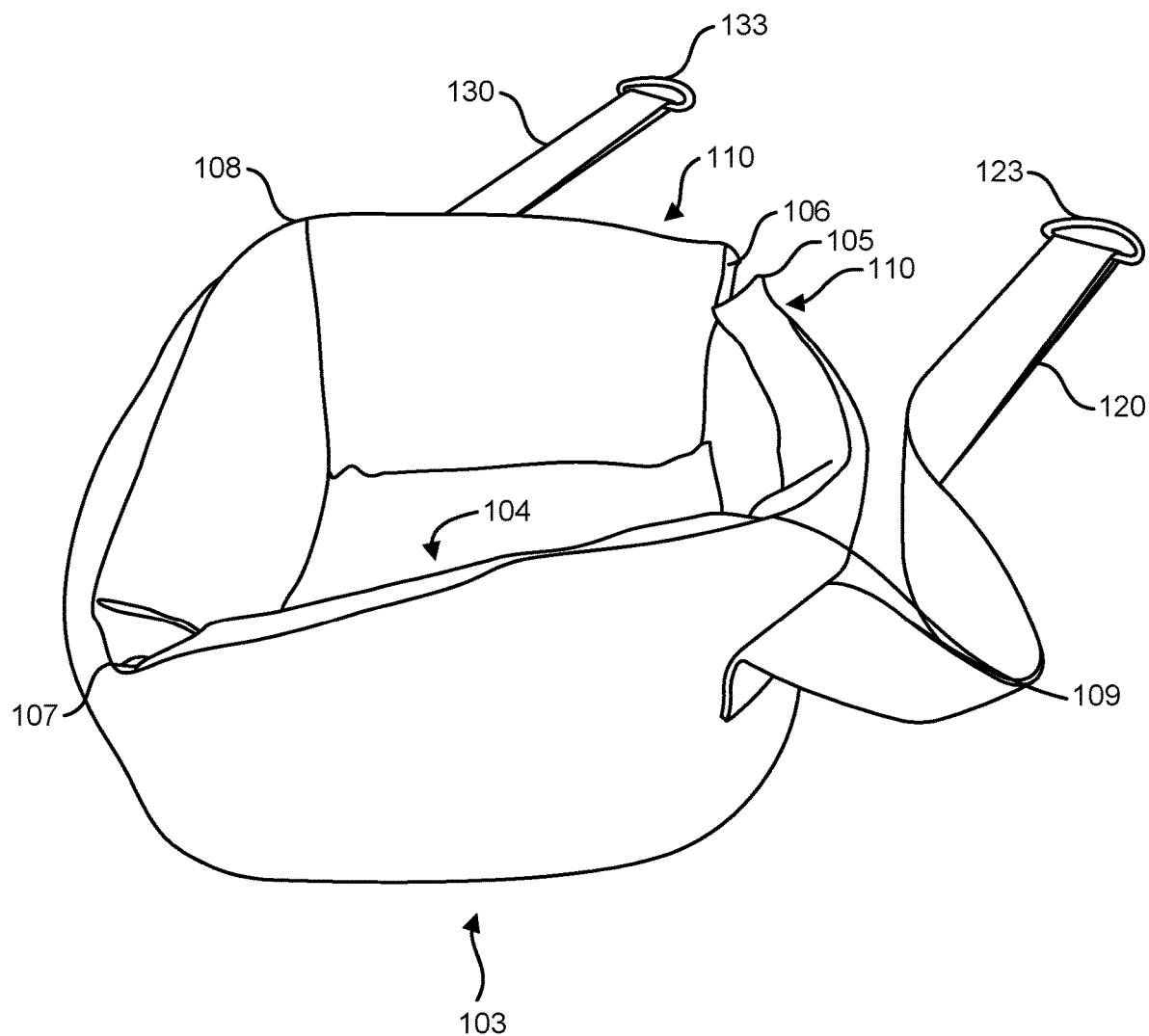
FIG. 2 is a perspective view of an embodiment of the present system with the fastener fastened so as to form the collar into a ring shape.

FIG. 1 is a plan view of an embodiment of the present traction system 100 where the collar is in an open position, laid flat such that the exterior is visible. FIG. 2 is a perspective view of an embodiment of the present system with the fastener connected to form a ring. As shown, the collar 101 includes a faster, 102a and 102b. In the embodiment of FIG. 1, 102a is the hook portion of a hook and loop fastener while 102b is the loop portion. It should be understood that the collar may be made of a fabric having sufficient nap that the hooks engage directly with the collar rather than requiring separate loops 102b. In the embodiment of FIG. 1, the collar includes a base 103 and a top 104, a first terminating edge 105 and a second terminating edge 106. The base may be substantially flat, and the top may be undulating. The distance between the base and the top may be referred to as the height. The terminating edges may be brought together and the fastener fastened to form a ring with the terminating edges at the back and the central chin dip 107 at the front. It should be understood that when the terminating edges are fastened together, the terminating edges themselves need not actually be connected or touching, but rather it is sufficient that the collar is simply held in its ring shape by the fastened fastener. It should be understood that terms like front, back, top, and bottom are used for reference regardless of orientation. For example, even if the chin dip is oriented at the back of the head when worn by a patient, and the terminating edges are positioned under the chin, the terminating edges may still be referred to as the back. The undulating top may include one or more peaks 108, 109, and a back dip 110 (formed when terminating edges 105, 106 are brought together). Preferably, the collar includes two peaks positioned one on either side of the collar when the fastener 102a, 102b is fastened, such that the peaks are between the chin dip 107 and back dip 110.

Two straps 120, 130 are connected to the exterior of the collar. For example, the proximal ends, 121, 131 of the straps may be sewn to the cover of the collar. The distal ends 122, 132 may remain loose. The distal ends may be woven or folded to form loops. The distal ends may also, or alternatively, include connectors, such as rings (or D-rings) 123, 133. It was found that nylon webbing was suitable for creating the straps, though other materials could be used.

Figure 3:
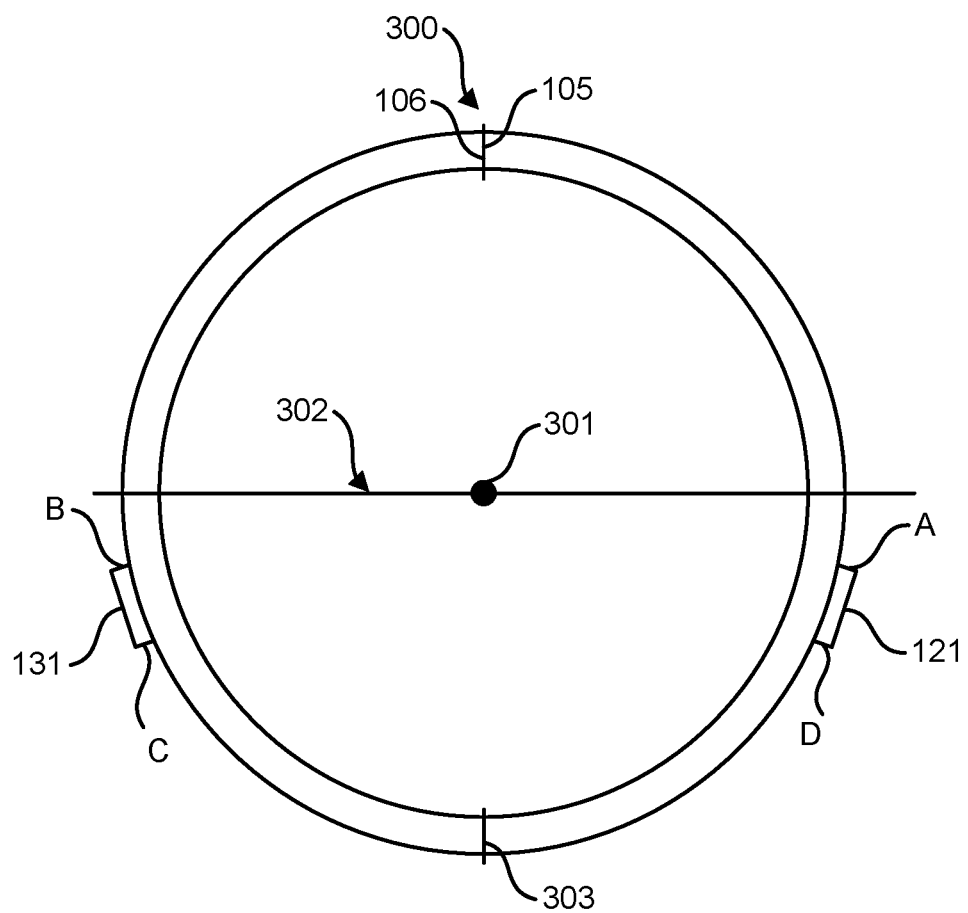
FIG. 3 is a top-down block diagram of an embodiment of the present system showing the spatial relationships between select components.
Figure 4:
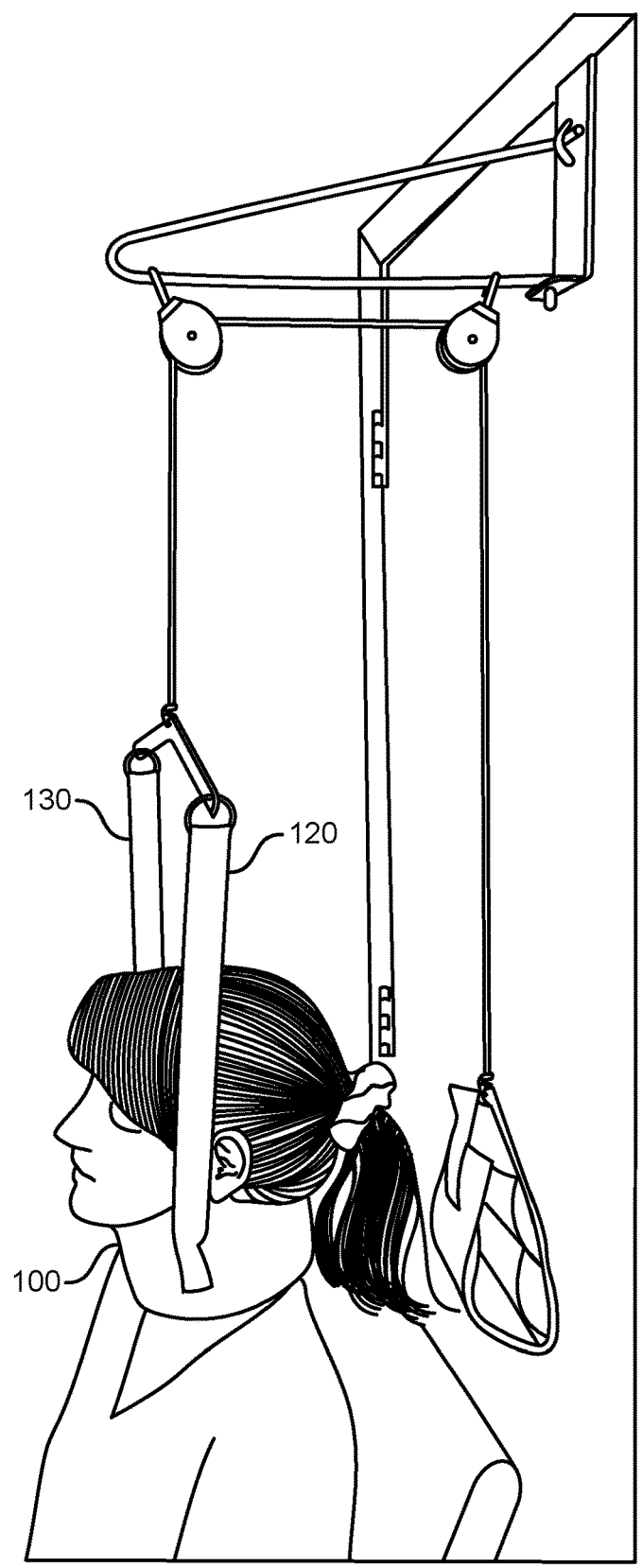
FIG. 4 is a side view of an embodiment of the system being worn by a patient and having traction force applied.

FIG. 3 is an illustrative block diagram of one embodiment of the collar viewed from the top down to show general spatial relationships between components of the system. The back is shown with the terminating edges 105, 106 connected and connection seam is designated as 300. The collar includes a midpoint, which is the point along the circumference that is equidistant from the seam. For example, in an embodiment where the length of the collar from terminating edge to terminating edge is 20 inches, the midpoint is 10 inches from the terminating edges. The center of the collar is identified as 301, and a center plane, dividing the collar into a top semicircle and bottom semicircle is identified as 302. The distal ends 121, 131 of the straps are shown connected to the exterior of the collar. In some embodiments the straps are between 0.5 and 2 inches wide. While the width could be different, it was found that straps having a width of approximately 1.0 inches provided sufficient strength and connection stability to provide adequate therapy without damaging the collar. In one embodiment, the straps are offset from the center plane 302 of the ring formed by the collar. While the collar could be made larger or smaller depending on the size of the patient, for an average adult, a collar having a total length (from terminating edge 105 to terminating edge 106) of approximately 20 inches was found to be sufficient. In one embodiment, the distance between the straps on the front of the collar is greater than the distance between the straps on the back of the collar. That is, the distance from point A to B, traveling along the back of the collar, is greater than the distance from point C to D traveling along the front of the collar. In one embodiment, the distance from A to B is approximately 10 inches, whereas the distance from C to D is approximately 8 inches. Thus, when the collar is positioned on a patent with the front positioned proximal to the chin and the seam 300 positioned proximal to the back of the head, the straps are positioned forward of the center plane 302. That orients the straps in front of the ears on an average adult. When a traction force is applied, a greater force is applied to the front, under the jaw, than at the back, such that the head is forced to tip backwards to even the pressure. This positioning in depicted in FIG. 4. It should be appreciated that the term "traction force" is used herein to refer to a pulling force on the straps and, by extension, the collar which is then communicated to the patient through the collar. Traction force is applied perpendicular to the plane of the circumference of the collar. That is, in an embodiment where the bottom is flat, such as is shown in FIG. 1, the plane of the circumference of the collar is coextensive with the plane of the bottom. The straps may be secured perpendicular to the plane of the circumference such that applying a straight pulling force to the straps applies the traction force to the collar in a manner that is perpendicular to the plane of the circumference of the collar. It should be appreciated that as the traction force is increased, in embodiments where the straps are offset from the center plane 302, the traction force will tend to skew from exact perpendicular as the collar tilts to even the application of force.

Figure 5:
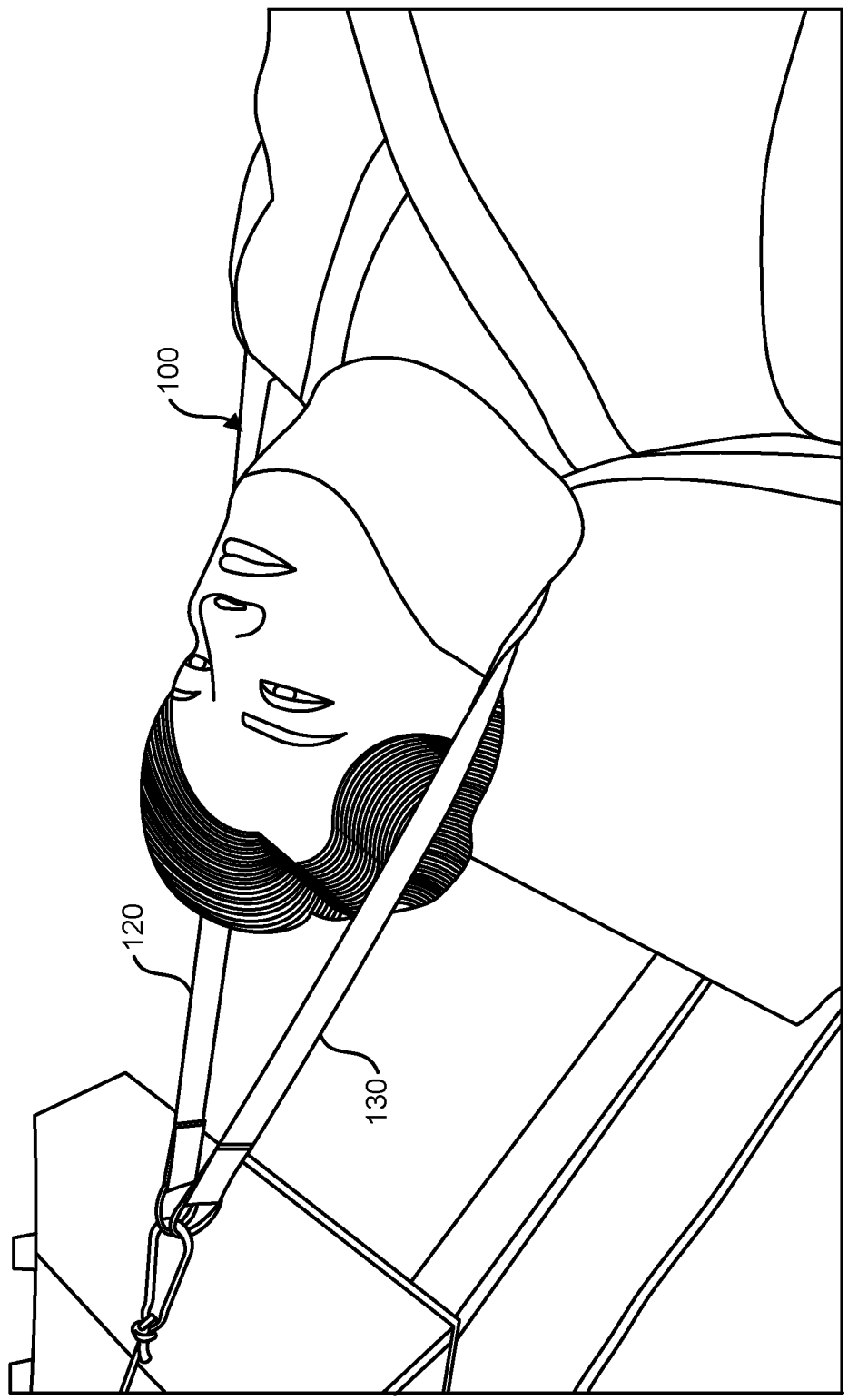
FIG. 5 is a perspective view of an embodiment of the system being worn by a patient and having traction force applied.

The collar may also be worn backward such that the straps are positioned further back, behind the ears on an average adult, see FIG. 5. In that position, when traction force is applied, a greater force is applied to the back of the collar, and back of the skull, such that the head tips forward to equalize the pressure. It should be appreciated that, whereas the straps are oriented below the central plane in FIG. 3, they could be positioned above the central plane such that the distance from A to B is shorter than the distance from C to D. In either case, the collar may be worn with seam proximal to the chin or the seam proximal to the back of the skull, and the position of the straps being offset from the center plan will allow the tension force applied to the straps to apply pressure that either slightly tilts the head backward or forward respectively.

The straps may be attached to the collar midway between the bottom and top. By placing the straps spaced apart from the top, when traction force is applied, the straps compress the foam of the collar against the patient. It was found that utilizing a foam having a thickness of approximately 1.0 inches provided comfortable therapy while maintaining the pressure of the straps oriented sufficiently close to the head without having the straps unnecessarily rub against the patient's cheeks or ears.

In one embodiment, as shown in FIG. 1, the collar may include an undulating top 104. The undulating top may include one or more peaks 108, 109, and a back dip 110 (formed when terminating edges 105, 106 are brought together). Preferably, the collar includes two peaks positioned one on either side of the collar when the fastener 102a, 102b is fastened, such that the peaks are between the chin dip 107 and back dip 110. The highest point of each peak is the apex, and the lowest point of each dip is the valley. It has been found that the distance from the base to the apex of each peak should be substantially equal to provide uniform stability of the head during traction. In one embodiment, the height of the apex is approximately 4.0 inches and the height of the valley of the chin dip 107 and back dip 110 is approximately 3.0 inches. In one embodiment, the height of the back valley is greater than the height of the front valley, for example, 3.5 inches where the front valley is 3.0 inches. In some embodiments, the top and bottom are each substantially flat and the height of the collar may be 2.0-4.0 inches. While other heights could be used, the foregoing generally fit the average adult body comfortably without putting pressure on the shoulders or clavicle.

Although the present invention has been described in terms of the preferred embodiments, it is to be understood that such disclosure is not intended to be limiting. Various alterations and modifications will be readily apparent to those of skill in the art. Accordingly, it is intended that the appended claims be interpreted as covering all alterations and modifications as fall within the spirit and scope of the invention.

What is claimed is:

1. A therapy device comprising:
    Aa collar comprising a top, a bottom, two terminating edges wherein when the terminating edges are brought together, the terminating edges form a seam and the collar is formed into a ring having an interior circumference, and exterior circumference, and a midpoint;
    a fastener connected to the collar proximate to at least one of the terminating edges and adapted to abut the terminating edges together; and
    a first strap connected to the exterior circumference of the collar;
    a seccond strap connected to the exterior circumference of the collar;
    wherein the seam is formed in a back half of the ring;
    wherein the first strap is connected to the collar on one side of the midpoint and the second strap is connected to the collar on another side of the midpoint; and
    wherein a back distance along the exterior circumference extending from the first strap to the second strap is greater than a front distance along the exterior circumference extending from the first strap to the second strap.

2. The therapy device of claim 1, wherein a distance along the exterior circumference from the seam to the first strap and a distance along the exterior circumference from the seam to the second strap are the equal and wherein the first strap is positioned closer to the midpoint than to the seam.

3. The therapy device of claim 1, wherein the first strap and second strap each include a proximal end and a distal end;
    wherein the proximal ends of the first and second straps are fastened to the exterior of the collar; and
    wherein the distal ends of the first and second straps each include a ring.

4. The therapy device of claim 1, wherein the collar comprises a foam material surrounded by a cover.

5. The therapy device of claim 1, wherein the exterior circumference of the collar is twenty inches.

6. The therapy device of claim 1, wherein the front distance along the exterior circumference eight inches.

7. A therapy device comprising:
    A collar comprising a top, a bottom, two terminating edges, wherein when the terminating edges are brought together, the terminating edges form a seam and the collar is formed into a ring having an interior circumference, and exterior circumference, and a midpoint;
    a fastener connected to the collar proximate to at least one of the terminating edges and adapted to abut the terminating edges together;
    a plurality of straps connected to the exterior circumference of the collar;
    wherein the top undulates,
    wherein the plurality of straps comprise a first strap and a second strap;
    wherein the seam is formed in a back half of the ring;
    wherein the first strap is connected to the collar on one side of the midpoint and the second, strap is connected to the collar on another side of the midpoint,
    wherein the midpoint is located at a valley of the undulating top;
    wherein the collar further comprises a first side and a second side such that each side of the collar extends from the midpoint to one of the terminating edges and includes at least one peak;
    wherein the first strap is connected to the collar such that it crosses a peak of the first side of the collar when a traction force is applied to the first strap; and
    wherein the second strap is connected to the collar such that it crosses a peak of the second side of the collar when traction force is applied to the second strap.

8. The therapy device of claim 7, wherein the first strap crosses an apex of the peak of the first side of the collar when the traction force is applied to the first strap; and
    wherein the second strap crosses the apex of the peak of the second side of the collar when the traction force is applied to the second strap.

9. A therapy device of claim 7,
    wherein the first peak includes a first apex and the second peak includes a second apex; and
    wherein a height of the collar at the midpoint is less than a height of the collar at either the apex of the first peak or the apex of the second peak.

10. A therapy device of claim 9, further comprising a back valley formed at the seam, wherein a height of the back valley is substantially the same as a height of the front valley.

11. The therapy device of claim 9 further comprising: a back valley formed at the seam, wherein a height of the back valley is greater than a height of the front valley but less than a height of either the apex of the first peak of the apex of the second peak.

12. A therapy device comprising
    a collar comprising a top, a bottom, two terminating edges, wherein when the terminating edges are brought together, the terminating edges form a seam and the collar is formed into a ring having an interior circumference, an exterior circumference, and a midpoint;
    a fastener connected to the collar proximate to at least one of the terminating edges and adapted to abut the terminating edges together;
    a plurality of straps connected to the exterior circumference of the collar;
    wherein the top undulates;
    wherein the undulating top comprises a front valley at the midpoint, a valley at the seam, a first peak located between the midpoint and a first terminating edge of the terminating edges, and
    a second peak located between the midpoint and a second terminating edge of the terminating edges;
    wherein the plurality of straps comprise a first strap and a second strap,
        wherein the first strap is secured to the collar such that it crosses the apex of the first peak when traction force is applied; and wherein the second strap is secured to the collar such that it crosses the apex of the second peak when traction force is applied.

13. The therapy device of claim 12, wherein a distance along the exterior circumference extending from the midpoint to either an apex of the first peak or an apex of the second peak is 4.5 inches.

14. The therapy device of claim 13, wherein a distance along the exterior circumference extending from the first terminating edge to the apex of the first peak is 5.5 inches; and wherein a distance along the exterior circumference extending from the first terminating edge to the apex of the second peak is 5.5 inches.

\* \* \* \* \*